United States Patent [19]

Meyer

[11] Patent Number: 5,306,693
[45] Date of Patent: Apr. 26, 1994

[54] SULFONYLUREAS

[75] Inventor: Willy Meyer, Riehen, Switzerland

[73] Assignee: Ciba-Geigy Corporation, Ardsley, N.Y.

[21] Appl. No.: 931,753

[22] Filed: Aug. 18, 1992

Related U.S. Application Data

[62] Division of Ser. No. 744,625, Aug. 12, 1991, Pat. No. 5,163,996.

[30] Foreign Application Priority Data

Aug. 15, 1990 [CH] Switzerland ............................ 2654/90

[51] Int. Cl.$^5$ .................... A01N 43/54; A01N 43/66; C07D 239/48; C07D 239/47
[52] U.S. Cl. .................................. 504/214; 544/321; 544/323; 544/332
[58] Field of Search .................... 71/92; 544/321, 323, 544/332; 504/214

[56] References Cited

U.S. PATENT DOCUMENTS 4,310,346  1/1982  Levitt et al. ............................ 71/92
4,452,628  6/1984  Adams ..................................... 71/92

OTHER PUBLICATIONS

"DuPont", Chemical Abstracts, vol. 107, entry 176061n (1987).
Hillemann, Chemical Abstracts, vol. 112, entry 179033u (1990).

Primary Examiner—John M. Ford
Attorney, Agent, or Firm—Kevin T. Mansfield; George R. Dohmann

[57] ABSTRACT

N-phenylsulfonyl-N'-pyrimidinyl- and -triazinyl-ureas of formula I

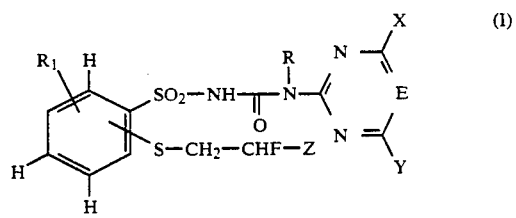

wherein
R is hydrogen or $C_1$-$C_4$alkyl,
$R_1$ is hydrogen, halogen, $C_1$-$C_5$alkyl, $C_2$-$C_5$alkenyl, $C_1$-$C_4$haloalkyl, COO—$R_2$ or A—$R_3$;
$R_2$ is $C_1$-$C_5$alkyl;
$R_3$ is $C_1$-$C_5$alkyl, $C_2$-$C_4$alkoxyalkyl or $C_1$-$C_5$haloalkyl;
X is $C_1$-$C_3$alkyl, $C_1$-$C_3$alkyl mono- to tri-substituted by halogen; $C_1$-$C_3$alkoxy or $C_1$-$C_3$alkoxy mono- to tri-substituted by halogen;
A is oxygen, sulfur, SO or $SO_2$;
Y is halogen, $C_1$-$C_3$alkyl, $C_1$-$C_3$alkyl mono- to tri-substituted by halogen; $C_1$-$C_3$alkoxy, $C_1$-$C_3$alkoxy mono- to tri-substituted by halogen; cyclopropyl, methylamino or dimethylamino;
E is nitrogen or the methine group; and
Z is fluorine or chlorine; and the salts of those compounds with amines, alkali or alkaline earth metal bases or with quaternary ammonium bases have good pre- and post-emergence selective herbicidal and growth-regulating properties.

15 Claims, No Drawings

SULFONYLUREAS

This is a division of Ser. No. 744,625 filed Aug. 12, 1991 now U.S. Pat. No. 5,163,996.

The present invention relates to novel herbicidally active and plant-growth-regulating N-phenylsulfonyl-N'-pyrimidinyl- and -triazinyl-ureas, to processes for the preparation thereof, to compositions comprising them as active ingredients, and to the use thereof for controlling weeds, especially selectively in crops of useful plants, or for regulating and inhibiting plant growth.

Phenylsulfonylureas having herbicidal action are known from European Patent Applications No. 0 044 808 and No. 0 072 347. The compounds specifically disclosed therein are not, however, always able to satisfy requirements in respect of potency and activity spectrum. There is accordingly a need for compounds having improved and more selective action.

Novel sulfonylureas having improved herbicidal and plant-growth-regulating properties have now been found.

The N-phenylsulfonyl-N'-pyrimidinyl- and -triazinyl-ureas according to the invention correspond to formula I

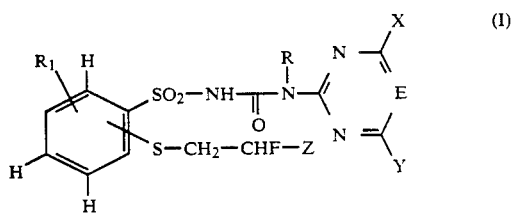

wherein

R is hydrogen or $C_1$-$C_4$alkyl;

$R_1$ is hydrogen, halogen, $C_1$-$C_5$alkyl, $C_2$-$C_5$alkenyl, $C_1$-$C_4$haloalkyl, COO—$R_2$ or A—$R_3$;

$R_2$ is $C_1$-$C_5$alkyl;

$R_3$ is $C_1$-$C_5$alkyl, $C_2$-$C_4$alkoxyalkyl or $C_1$-$C_5$haloalkyl;

X is $C_1$-$C_3$alkyl, $C_1$-$C_3$alkyl mono- to tri-substituted by halogen; $C_1$-$C_3$alkoxy or $C_1$-$C_3$alkoxy mono- to tri-substituted by halogen;

A is oxygen, sulfur, SO or $SO_2$;

Y is halogen, $C_1$-$C_3$alkyl, $C_1$-$C_3$alkyl mono- to tri-substituted by halogen; $C_1$-$C_3$alkoxy, $C_1$-$C_3$alkoxy mono- to tri-substituted by halogen; cyclopropyl, methylamino or dimethylamino;

E is nitrogen or the methine group; and

Z is fluorine or chlorine;

and the salts of those compounds.

The alkyl groups occurring in the definitions of the substituents may be straight-chained or branched and are, for example, methyl, ethyl, n-propyl, isopropyl, n-butyl, sec-butyl, isobutyl, tert-butyl, n-pentyl or the isomers of pentyl. Within the scope of the present invention, alkyl is preferably methyl or ethyl.

Halogen is to be understood as being fluorine, chlorine, bromine or iodine, preferably fluorine or chlorine.

Haloalkyl is, for example, trifluoromethyl, 1-fluoroethyl, 1,1-dichloroethyl, 3,3,3-trifluoropropyl, 2-fluoroisopropyl, 3-fluoropropyl, 1,1,1-trichloropentyl, 1-fluoro-3-methylpentyl, or 1-bromohexyl.

Examples of alkoxyalkyl are: methoxymethyl, methoxyethyl, methoxypropyl, ethoxymethyl, ethoxyethyl and propoxymethyl.

The $C_1$-$C_3$alkyl radicals occurring as or in the substituents X and Y include, in particular, methyl, ethyl, n-propyl and isopropyl and also the haloalkyl radicals that are derived from those radicals and are mono- to tri-substituted by halogen. The alkyl radicals occurring as or in the substituents X and Y preferably have one or two carbon atoms.

Of the $C_1$-$C_3$alkyl groups that occur as or in the substituents X and Y and are mono- to tri-substituted by halogen, $C_1$-$C_2$alkyl groups mono- to tri-substituted by fluorine or chlorine are preferred. Especially preferred $C_1$-$C_3$alkyl radicals that occur as or in the substituents X and Y and are mono- to tri-substituted by halogen are: trifluoromethyl, difluoromethyl, 2-chloroethyl, chlorodifluoromethyl, dichloromethyl, chlorofluoromethyl, 1,1-dichloroethyl, trifluoroethyl, 3,3,3-trifluoropropyl and 2,3-dichloropropyl, with fluoromethyl, chloromethyl, difluoromethyl and trifluoromethyl being particularly preferred.

The $C_2$-$C_5$alkenyl radicals occurring in the substituent $R_1$ may be in the Z form (cis) or in the E form (trans) and may be straight-chained or branched. Alkenyl radicals having a chain length of two or three carbon atoms are preferred. Examples of $C_2$-$C_5$alkenyl radicals are: vinyl, allyl, methallyl, 1-methylvinyl, 2-methylvinyl, but-2-en-1-yl and pent-3-en-1-yl. Vinyl and allyl are preferred.

The invention also includes the salts that the compounds of formula I can form with amines, alkali and alkaline earth metal bases or quaternary ammonium bases.

Of the alkali and alkaline earth metal hydroxides as salt-formers, prominence is to be given to the hydroxides of lithium, sodium, potassium, magnesium and calcium, but especially to the hydroxides of sodium and potassium.

Examples of amines that are suitable for salt formation are primary, secondary and tertiary aliphatic and aromatic amines, such as methylamine, ethylamine, propylamine, isopropylamine, the four isomers of butylamine, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, but especially ethyl-, propyl-, diethyl- or triethyl-amine, and more especially isopropylamine and diethanolamine.

Examples of quaternary ammonium bases are generally the cations of haloammonium salts, for example the tetramethylammonium cation, the trimethylbenzylammonium cation, the triethylbenzylammonium cation, the tetramethylammonium cation and the trimethylethylammonium cation, but also the ammonium cation.

Preferred compounds of formula I are those wherein $R_1$ at the phenyl ring is in the 5-position and the group —S—$CH_2$—CHF—Z is in the 2-position.

Other preferred compounds of formula I are those wherein $R_1$ and/or R are (is) hydrogen.

Very especially preferred groups of compounds of formula I are those wherein a) X is $C_1$-$C_3$alkyl, $C_1$-$C_3$alkoxy or $C_1$-$C_3$alkoxy mono- to tri-substituted by halogen; and Y is chlorine, $C_1$-$C_3$alkyl, $C_1$-$C_3$alkoxy, cyclopropyl, or $C_1$-$C_3$alkoxy mono- to tri-substituted by halogen; or b) X is methyl, methoxy, ethoxy or difluoromethoxy; and Y is methyl, methoxy, ethoxy, difluoromethoxy or chlorine; or c) X is methoxy or ethoxy; and Y is methyl or methoxy; or d) E is nitrogen.

A group of compounds of formula I that is especially prominent owing to its good biological activity is that wherein $R_1$ is hydrogen and X is $C_1$-$C_3$alkyl, $C_1$-$C_3$alkoxy or $C_1$-$C_3$alkoxy mono- to tri-substituted by halogen; and Y is chlorine, $C_1$-$C_3$alkyl, $C_1$-$C_3$alkoxy, cyclopropyl, or $C_1$-$C_3$alkoxy mono- to tri-substituted by halogen. Preferred among this group are also those compounds of formula I wherein X is methyl, methoxy, ethoxy or difluoromethoxy and Y is methyl, methoxy, ethoxy, difluoromethoxy or chlorine, the meanings methoxy and ethoxy being very especially preferred for X and the meanings methyl and methoxy being very especially preferred for Y. In this outstanding group of compounds, $R_1$ at the phenyl ring is preferably in the 5-position and the group —S—CH$_2$—CBF—Z is preferably in the 2-position.

The following may be mentioned as preferred individual compounds within the scope of formula I:
N-(2-(2-chloro-2-fluoroethylthio)-phenyl-sulfonyl)-N'-(4-methoxy-6-methyl-1,3,5-triazin-2-yl)-urea; and
N-(2-(2,2-difluoroethylthio)-phenyl-sulfonyl)-N'-(4-methoxy-6-methyl-1,3,5-triazin-2-yl)-urea.

The compounds of formula I can be prepared by
a) reacting a phenylsulfonamide of formula XIV

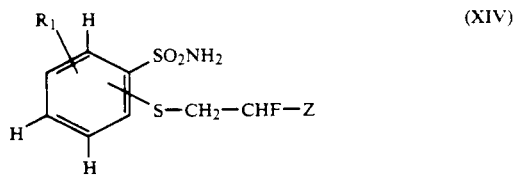

wherein $R_1$ and Z are as defined under formula I, in the presence of a base, with an N-pyrimidinyl or N-triazinyl carbamate of formula XI

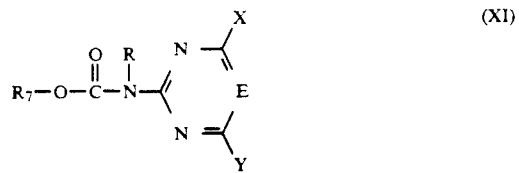

wherein X, Y, R and E are as defined under formula I and $R_7$ is $C_1$-$C_4$alkyl, or phenyl which may be substituted by $C_1$-$C_4$alkyl or by halogen; or b) reacting a phenylsulfonamide of formula XII

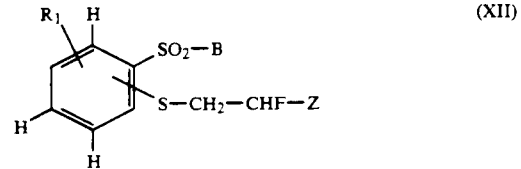

wherein $R_1$ and Z are as defined in formula I, and B is

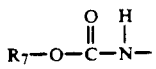

or O=C=N—, in the presence of a base, with a 2-amino-pyrimidine or -triazine of formula XIII

wherein E, X and Y are as defined under formula I.

The reactions to form compounds of formula I are advantageously carried out in aprotic, inert organic solvents. Such solvents are hydrocarbons, such as benzene, toluene, xylene or cyclohexane, chlorinated hydrocarbons, such as dichloromethane, trichloromethane, tetrachloromethane or chlorobenzene, ethers, such as diethyl ether, ethylene glycol dimethyl ether, diethylene glycol dimethyl ether, tetrahydrofuran or dioxane, nitriles, such as acetonitrile or propionitrile, amides, such as dimethylformamide, diethylformamide or N-methylpyrrolidone. The reaction temperatures are preferably from −20° to +120° C.

The reactions generally proceed in a slightly exothermic manner and can be carried out at room temperature. In order to reduce the reaction time or also to initiate the reaction, it is expedient to heat the reaction mixture briefly at boiling point. The reaction times can also be reduced by adding a few drops of base as a reaction catalyst. Suitable bases are especially tertiary amines, such as trimethylamine, triethylamine, quinuclidine, 1,4-diazabicyclo(2.2.2)octane, 1,5-diazabicyclo(4.3.0)non-5-ene or 1,5-diazabicyclo(5.4.0)undec-7-ene. Other bases that may be used, however, are inorganic bases, such as hydrides, such as sodium or calcium hydride, hydroxides, such as sodium and potassium hydroxide, carbonates, such as sodium and potassium carbonate, or hydrogen carbonates, such as potassium and sodium hydrogen carbonate.

The end products of formula I can be isolated by concentration and/or evaporation of the solvent and can be purified by recrystallisation or trituration of the solid residue in solvents in which they are not readily soluble, such as ethers, aromatic hydrocarbons or chlorinated hydrocarbons.

The intermediates of formulae XI, XII and XIII are known or can be prepared analogously to known processes. Processes for the preparation of N-pyrimidinyl and N-triazinyl carbamates are described, for example, in EP-A-0 101 670. Processes for the preparation of the compounds of formula XII are described in EP-A-0 044 808. Compounds of formula XIII are known from EP-A-0 070 804.

The compounds of formula XIV can be prepared by
a) converting a 2-halophenylsulfonamide of formula II

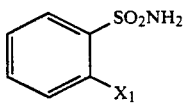 (II)

wherein $X_1$ is fluorine, chlorine or bromine, in the presence of a base, with a mercaptan of formula III

 (III)

wherein $R_5$ is $C_1$-$C_6$alkyl or $C_1$-$C_6$alkyl substituted by phenyl, into a 2-sulfenylphenylsulfonamide of formula IV

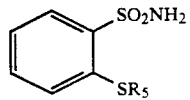 (IV)

wherein $R_5$ is as defined under formula III, b) oxidising that compound to the 2-sulfinylphenylsulfonamide of formula V

 (V)

wherein $R_5$ is as defined under formula III, c) reacting the resulting 2-sulfinylphenylsulfonamide of formula V in the presence of an acid to form the disulfide of formula VI

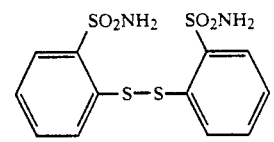 (VI)

d) reducing the disulfide of formula VI to the 2-mercaptophenylsulfonamide of formula VII

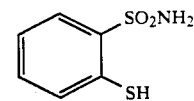 (VII)

e) then converting that compound using a trialkylamine of formula X $(R_6)_3N$ (X)

wherein $R_6$ is $C_1$-$C_4$alkyl, into the 2-mercaptophenylsulfonamide trialkylamine salt of formula VIII

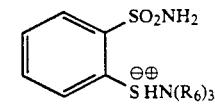 (VIII)

wherein $R_6$ is as defined under formula X, and f) then reacting that compound with a halofluoroethane of formula IX $Y_1$—$CH_2CHF$—$Z$ (IX)

wherein $Y_1$ is chlorine or bromine and Z is fluorine or chlorine.

The compounds of formulae II, III, IV, V, VII and IX are known and some of them are commercially available.

The disulfides of formula VI and the 2-mercaptophenylsulfonamide trialkylamine salts of formula VIII are the subject of Swiss Patent Application No. 3 554/89-5.

The $C_1$-$C_6$alkyl groups occurring in the substituent $R_5$ may be straight-chained or branched and are, for example, methyl, ethyl, n-propyl, isopropyl, n-butyl, sec-butyl, isobutyl, tert-butyl, n-pentyl or the isomers of pentyl, n-hexyl or the isomers of hexyl. The alkyl groups occurring in the substituent $R_5$ preferably have from 1 to 3 carbon atoms. If the alkyl groups are substituted by phenyl, they preferably have a chain length of from 1 to 3 carbon atoms. The substituent $R_5$ is especially preferably benzyl.

The $C_1$-$C_4$alkyl groups occurring in the substituents $R_6$ may be straight-chained or branched and are methyl, ethyl, n-propyl, isopropyl, n-butyl, sec-butyl or tert-butyl. $R_6$ is in each case especially preferably ethyl.

Process step a) is advantageously carried out in an inert solvent at a temperature of from 20° C. to the boiling temperature of the solvent. The temperatures are usually from +20° to +180° C., preferably from +20° to +120° C. An especially preferred temperature range is from +50° to +70° C.

Suitable solvents are chlorinated hydrocarbons, such as dichloromethane, trichloromethane, trichloroethane or tetrachloroethane, chlorobenzene or dichlorobenzene; aromatic hydrocarbons, such as benzene, toluene or xylene; ethers, such as diethyl ether, diisopropyl ether, tetrahydrofuran or dioxane; nitriles, such as acetonitrile or propionitrile; cyclohexane, pyridine, N-methylpyrrolidone or N,N-dimethylformamide, N,N-dimethylformamide being especially preferred.

The bases used are especially hydrides, hydroxides, carbonates or alcoholates of an alkali metal or of an alkaline earth metal, a trialkylamine or a pyridine base. Especially preferred bases are pyridine, sodium hydroxide, sodium methoxide, sodium ethoxide, sodium carbonate or potassium carbonate. Potassium carbonate is very especially preferred.

Process step a) can be carried out in an especially advantageous manner when 2-fluorophenylsulfonamide is used as the 2-halophenylsulfonwnide of formula II.

Permanganates, periodates, per-acids or hydrogen peroxide are especially suitable as oxidising agents for process step b).

Preferred oxidising agents are peracetic acid, perbenzoic acid, periodic acid, potassium permanganate, potassium periodate and hydrogen peroxide. A very especially preferred oxidising agent is hydrogen peroxide. The oxidation of the 2-sulfenylphenylsulfonamide of formula IV is advantageously carried out at temperatures of from 0° to +80° C., a temperature range of from 0° to +40° C. being preferred.

In a preferred variant of the process for the preparation of the compounds of formula II, the oxidation of the 2-sulfenylphenylsulfonamide of formula IV is carried out with hydrogen peroxide in the presence of acetic acid at a temperature of from +5° to +15° C.

Process variant c) is preferably carried out at a temperature of from +20° C. to the boiling temperature of the solvent. Solvents that have proved to be especially suitable are alcohols having a chain length of from 1 to 4 carbon atoms, for example methanol, ethanol, propanol, isopropanol, butanol or 2-butanol. A preferred solvent is methanol.

Acid-catalysed rearrangements of sulfoxides are known in the literature under the name "Pummerer rearrangements". Examples of such reactions can be found in Adv. Org. Chem. 6, 356 (1969). Contrary to the learning known from that article, the acid-catalysed rearrangement of the 2-sulfinylphenylsulfonamide of formula V does not result in 2-mercaptophenylsulfonamide but in 2,2'-bis-aminosulfonyl-diphenyl-disulfide of formula VI which can be isolated from its reaction medium in a simple manner and has a high degree of storage stability.

The nature of the acids used as catalysts in the reaction is not critical. Preferred acids are mineral acids, especially hydrochloric acid or sulfuric acid.

Process steps b) and c) can also be carried out in direct succession in a reaction vessel without isolating the intermediate of formula V. The solvents suitable for that process variant correspond to those mentioned in stage c).

The reductive cleavage of the disulfide of formula VI to form the 2-mercaptophenylsulfonamide of formula VIII (process step d)) is generally carried out at temperatures of from +20° C. to +100° C.

The reduction is preferably carried out with hydrogen in the presence of noble metal catalysts, or with zinc, iron or tin in the presence of hydrochloric acid or acetic acid, or with sodium, magnesium or aluminium amalgam. Preferred reducing agents are hydrogen in the presence of platinum, palladium, rhodium or nickel catalysts and also zinc, iron and tin in the presence of hydrochloric acid or acetic acid. A very especially preferred reducing agent is zinc in the presence of hydrochloric acid or acetic acid.

A trialkylamine of formula X that is especially suitable for salt formation in accordance with process step e) is triethylamine.

The reaction temperatures for the reaction of the 2-mercaptophenylsulfonamide trialkylamine salts with the halofluoroethane of formula IX (process step f)) are from 0° to 80° C., preferably from 0° to +40° C. The reaction proceeds in an especially advantageous manner when $Y_1$ in formula IX is bromine. The solvents suitable for stage f) correspond to those mentioned in stage a).

The compounds of formula I are generally used successfully at rates of application of from 0.001 to 2 kg/ha, especially from 0.005 to 1 kg/ha. The concentration required to achieve the desired effect can be determined by experiment. It is dependent on the type of action, the stage of development of the cultivated plant and of the weed, and also on the application (place, time, method) and, in dependence on those parameters, can vary within wide limits.

When used at relatively low rates of application, the compounds of formula I are distinguished by growth-inhibiting and herbicidal properties, which render them excellently suitable for use in crops of useful plants, especially in cereals, cotton, soybeans, rape, maize and rice, their use in cereals being very especially preferred.

The invention relates also to herbicidal and plant-growth-regulating compositions comprising a novel compound of formula I, and to methods of inhibiting plant growth.

Plant growth regulators are substances that bring about agronomically desirable biochemical and/or physiological and/or morphological changes in/to the plant.

The active ingredients comprised by the compositions according to the invention influence plant growth in different ways depending on the time of application, the concentration, the type of application and the environmental conditions. Plant growth regulators of formula I can, for example, inhibit the vegetative growth of plants. Ibis type of action is valuable in the case of lawn areas, in the cultivation of ornamentals, in fruit plantations, in the case of roadside embankments and in sports fields and industrial sites, but also in the specific inhibition of side-shoots, as in the case of tobacco. In agriculture, inhibition of the vegetative growth of cereals leads, owing to a strengthening of the stalk, to reduced lodging, and similar agronomic effects are achieved in rape, sunflowers, maize and other cultivated plants. Moreover, by inhibiting the vegetative growth it is possible to increase the number of plants per unit area. Another field of application for growth inhibitors is the selective control of cover plants in plantations or widely spaced crops by greatly inhibiting the growth of the cover crops without killing them, so that competition with the main crop is eliminated but the agronomically positive effects, such as erosion prevention, fixing of nitrogen and loose soil structure, are preserved.

A method of inhibiting plant growth is to be understood as being a method of controlling a plant's natural development without changing its life-cycle, as determined by genetic characteristics, in the sense of mutation. The method of regulating growth is applied at a time in the plant's development that has to be determined for each individual case. The compounds of formula I can be applied pre- or post-emergence, for example to the seeds or seedlings, to roots, tubers, stalks, leaves, blossoms or other parts of the plant. This can be done, for example, by applying the compound as such or in the form of a composition to the plants, and/or by treating the plant's nutrient medium (soil).

Various methods and techniques are suitable for the use of the compounds of formula I or of compositions containing them for regulating plant growth, for example the following:

i) Seed dressing a) Dressing the seeds with an active ingredient formulated as a wettable powder, by shaking in a container until the formulation is uniformly distributed over the surface of the seeds (dry dressing). Up to 4 g of compound of formula I (in the case of a 50% formulation: up to 9.0 g of wettable powder) are used per 1 kg of seed.

b) Dressing the seeds with an emulsifiable concentrate of the active ingredient or with an aqueous solution of the compound of formula I formulated as a wettable powder according to method a) (wet dressing).

c) Dressing by soaking the seeds for a period of from 1 to 72 hours in a liquor containing up to 1000 ppm of compound of formula I and, if desired, subsequently drying the seeds (seed soaking).

Seed dressing or treatment of the germinated seedling are naturally the preferred methods of application because the treatment with the active ingredient is then directed wholly at the target crop. From 0.001 g to 4.0 g of active ingredient are normally used per 1 kg of seed, although, depending on the method employed, which also allows the addition of other active ingredients or micronutrients, amounts that exceed or fan short of the specified concentration limits may be employed (repeat dressing).

ii) Controlled release of active ingredient

A solution of the active ingredient is applied to mineral granulated carriers or polymerised granules (urea-/formaldehyde) and allowed to dry. If required, a coating may be applied (coated granules), which allows the active ingredient to be released in metered amounts over a specific period of time.

The compounds of formula I are used in unmodified form, as obtainable from synthesis, or, preferably, as compositions together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures containing the compound (active ingredient) of formula I and, where appropriate, one or more solid or liquid adjuvants, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloahpatic hydrocarbons such as paraffins, cyclohexane or tetrahydronaphthalene; alcohols such as ethanol, propanol or butanol; glycols and their ethers and esters, such as propylene glycol or dipropylene glycol ether, ketones such as cyclohexanone, isophorone or diacetone alcohol, strongly polar solvents such as N-methyl-2-pyrrolidone, dimethyl sulfoxide or water; vegetable oils and their esters, such as rape oil, castor oil or soybean oil; and, where appropriate, also silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylarylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or hydrogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylarnmonium bromide.

The surfactants customarily employed in formulation technology are described inter alia in the following publications:

"Mc Cutcheon's Detergents and Emulsifiers Annual", Mc Publishing Corp., Glen Rock, N.J. 1988.

M. and J. Ash, "Encyclopedia of Surfactants", Vol. I–III, Chemical Publishing Co., New York, 1980–1981.

Dr. Helmut Stache "Tensid-Taschenbuch", Carl Hanser Verlag, Munich/Vienna 1981.

The herbicidal compositions generally comprise 0.1 to 99%, preferably 0.1 to 95%, of a compound of formula I, 1 to 99% of a solid or liquid adjuvant and 0 to 25%, preferably 0.1 to 25%, of a surfactant.

Whereas commercial products will preferably be formulated as concentrates, the end user will normally employ dilute formulations.

The compositions may also comprise further additives such as stabilisers, for example vegetable oils and epoxidised vegetable oils (epoxidised coconut oil, rape oil or soybean oil), antifoams, for example silicone oil, preservatives, viscosity regulators, binders, tackifiers as well as fertilisers or other active ingredients for obtaining special effects.

Preferred formulations are composed in particular of the following constituents (throughout, percentages are by weight):

Emulsifiable concentrates:
active ingredient: 1 to 90%, preferably 5 to 20%
surfactant: 1 to 30%, preferably 10 to 20%
liquid carrier: 5 to 94%, preferably 70 to 85%

Dusts:
active ingredient: 0.1 to 10%, preferably 0.1 to 1%
solid carrier: 99.9 to 90%, preferably 99.9 to 99%

Suspension concentrates:
active ingredient: 5 to 75%, preferably 10 to 50%
water: 94 to 24%, preferably 88 to 30%
surfactant: 1 to 40%, preferably 2 to 30%

Wettable powders:
active ingredient: 0.5 to 90 preferably 1 to 80%
surfactant: 0.5 to 20 preferably 1 to 15%
solid carrier: 5 to 95%, preferably 15 to 90%

Granules:
active ingredient: 0.5 to 30%, preferably 3 to 15%
solid carrier: 99.5 to 70%, preferably 97 to 85%

PREPARATION EXAMPLES

EXAMPLE P1

Preparation of 2-benzylthiophenylsulfonamide

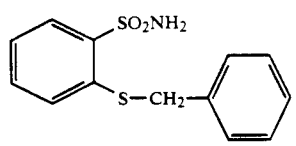

175.2 g of 2-fluorophenylsulfonamide and 160 g of potassium carbonate are added to a solution of 124.2 g of benzylmercaptan in 400 ml N,N-dimethylformamide. The reaction mixture is then heated at +60° C. for 3 hours. When the mixture has cooled to +25° C. it is filtered and the filtrate is then concentrated by evaporation.

1500 ml of water are added to the resulting residue, the product precipitating in the form of colourless crystals. After separating the solution off, the resulting crystals are dissolved in ethyl acetate and then treated with magnesium sulfate. After filtering and then concentrating the filtrate by evaporation, 219 g (78.5% of the theoretical yield) of 2-benzylthiophenylsulfonamide are obtained in the form of colourless crystals having a melting point of from +104° to +106° C.

EXAMPLE P2

Preparation of 2-benzylsulfinylphenylsulfonamide

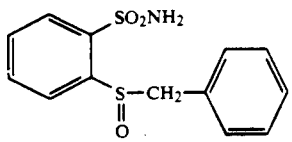

102 ml of 30% hydrogen peroxide solution are added dropwise at a temperature of +10° C. to a solution of 219 g of 2-benzylthiophenylsulfonamide obtained in accordance with Example P1 in 500 ml of concentrated acetic acid. The reaction mixture is then stirred for 5 hours at a temperature of +25° C., the product slowly crystallising out. After separating off the crystals, washing with water and drying, 219 g (94.6%) of 2-benzylsulfinylphenylsulfonamide are obtained in the form of colourless crystals having a melting point of from +206° to +209° C.

EXAMPLE P3

Preparation of 2,2'-bis-aminosulfonyl-diphenyl-disulfide

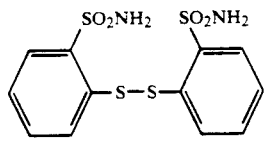

500 ml of concentrated hydrochloric acid are added to a solution of 214 g of a 2-benzylsulfinylphenylsulfonamide prepared in accordance with Example P2 in 500 ml of methanol. After boiling the reaction mixture for 7 hours and maintaining the mixture at room temperature for 2 days, the precipitated disulfide is separated off and washed with water, isopropanol and diethyl ether to yield 133.2 g (97.7% of the theoretical yield) of 2,2'-bis-aminosulfonyl-diphenyl-disulfide in the form of yellowish crystals having a melting point of +217° C, (decomposition).

EXAMPLE P4

Preparation of 2,2'-bis-aminosulfonyl-diphenyl-disulfide

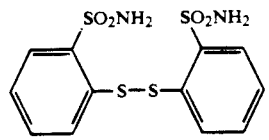

50 ml of concentrated hydrochloric acid and 3.5 g of 30% hydrogen peroxide solution are added dropwise to a solution of 10 g of 2-benzylthiophenylsulfonamide obtained in accordance with Example P1 in 50 ml of ethanol. The reaction mixture is then heated under reflux for a period of 1 hour. After cooling to +25° C., the crystals formed are separated off and washed with isopropanol and petroleum ether to yield 4 g of 2,2'-bis-aminosulfonyl-diphenyl-disulfide in the form of yellow

EXAMPLE P5

Preparation of 2-mercaptophenylsulfonamide

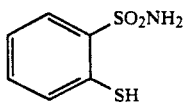

(VII)

18 g of zinc powder are added to a suspension of 23.2 g of a 2,2'-bis-aminosulfonyl-diphenyl-disulfide obtained in accordance with Examples P3 and P4 in 180 ml of concentrated acetic acid and the suspension is heated under reflux for 30 minutes. It is then cooled to +17° C. and filtered. After washing the filter residue with ethyl acetate, the filtrate is concentrated by evaporation and the residue is then dissolved in 200 ml of ethyl acetate. After washing twice with 100 ml of water each time and drying with magnesium sulfate, the solution is concentrated by evaporation to yield 22 g (94% of the theoretical yield) of unpurified 2-mercaptophenylsulfonamide having a melting point of from +113° to 140° C.

EXAMPLE P6

Preparation of the triethylamine salt of 2-mercaptophenylsulfonamide

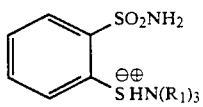

(VIII)

5 g of triethylamine are added dropwise at a temperature of +25° C. to a solution of 7.6 g of 2-mercaptosulfonamide obtained in accordance with Example P5 in 60 ml of tetrahydrofuran. The precipitated colourless crystals are then separated off and washed with diethyl ether to yield 9.2 g of the triethylamine salt of 2-mercaptophenylsulfonamide which has a melting point of from +164° to +168° C.

EXAMPLE P7

Preparation of 2-(2,2-difluoroethylthio)-phenyl-sulfonamide

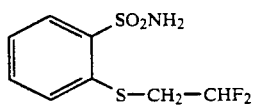

A mixture of 145.2 g of the triethylamine salt of 2-mercaptophenylsulfonamide obtained in accordance with Example P6 and 79.7 g of 2-bromo- 1,1 -difluoroethane in 600 ml of methanol is stirred for 16 hours at a temperature of from +55° C. to +60° C. The reaction mixture is then concentrated by evaporation. The residue is stirred with ice-water and the resulting suspension is filtered to yield 120 g (95% of the theoretical yield) of 2-(2,2-difluoroethylthio)-phenyl-sulfonamide having a melting point of from +111° C. to +112° C.

EXAMPLE P8

Preparation of 2-(2-chloro-2-fluoroethylthio)-phenylsulfonamide

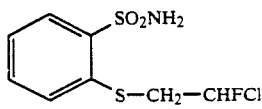

A mixture of 217.8 g of the triethylamine salt of 2-mercaptophenylsulfonamide obtained in accordance with Example P6 and 101 g of 1,2-dichloro-1-fluoroethane in 950 ml of methanol is stirred in an autoclave for 24 hours at a temperature of from +65° C. to +70° C. and for a further 24 hours at from +95° C. to +100° C. The reaction mixture is then concentrated by evaporation and the residue is stirred with water. By extracting with ethyl acetate, washing with water, drying over sodium sulfate, concentrating by evaporation and purifying the residue by chromatography with methylene chloride, 99.5 g (49.2% of the theoretical yield) of 2-(2-chloro-2-fluoroethylthio)-phenylsulfonamide having a melting point of from +88° C. to +89° C. are obtained.

EXAMPLE 9

Preparation of N-(2-(2-chloro-2-fluoroethylthio)-phenylsulfonyl)-N'-(4-methoxy-6-methyl-1,3,5-triazin-2-yl)-urea (Compound No. 1.001)

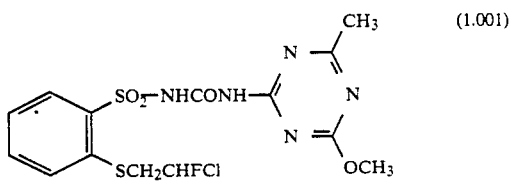

(1.001)

A solution of 1.07 g of 1,8-diazabicyclo[5.4.0]undec-7-ene in 10 ml of absolute dioxane is added dropwise at a temperature of from +20° to +25° C. to a mixture of 1.9 g of 2-(2-chloro-2-fluoroethylthio)-phenylsulfonamide and 1.85 g of N-(4-methyl-6-methoxy-1,3,5-triazin-2-yl)-phenyl carbamate in 40 ml of absolute dioxane. The reaction mixture is then stirred for 6 hours and subsequently added to water. After acidifying with 10% hydrochloric acid, extracting with ethyl acetate, washing with water and drying over sodium sulfate, the reaction mixture is filtered. Concentration of the filtrate by evaporation and recrystallisation of the residue from ethyl acetate yield 2.4 g of N-(2-(2-chloro-2-fluoroethylthio)-phenylsulfonyl)-N'-(4-methoxy-6-methyl-1,3,5-triazin-2-yl)-urea (Compound No. 1.001) having a melting point of from +174° to +176° C.

EXAMPLE P10

Preparation of N-(2-(2,2-difluoroethylthio)-phenylsulfonyl)-N'-(4-methoxy-6-methyl-1,3,5-triazin-2-yl)-urea (Compound No. 1.008)

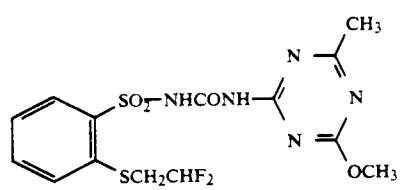

(1.008)

A solution of 1.07 g of 1,8-diazabicyclo[5.4.0]undec-7-ene in 10 ml of absolute dioxane is added dropwise at a temperature of from +20° to +25° C. to a mixture of 1.77 g of 2-(2,2-difluoroethylthio)-phenylsulfonamide and 1.82 g of N-(4-methyl-6-methoxy-1,3,5-triazin-2-yl)-phenyl carbamate in 40 ml of absolute dioxane. The reaction mixture is then stirred for 6 hours and subsequently added to water. After acidifying with 10% hydrochloric acid, extracting with ethyl acetate, washing with water and drying over sodium sulfate, the reaction mixture is filtered. Concentration of the filtrate by evaporation and recrystallisation of the residue from ethyl acetate yield 2.3 g of N-(2-(2,2-difluoroethylthio)-phenylsulfonyl)-N'-(4-methoxy-6-methyl-1,3,5-triazin-2-yl)-urea (Compound No. 1.001) having a melting point of from +189° to +190° C.

The compounds of formula I listed in the following Table are prepared in an analogous manner:

TABLE 1

Compounds of formula I:

$$\text{(I)}$$

| Comp. No. | Z | R | R₁ | Y | X | E | m.p. [°C.] |
|---|---|---|---|---|---|---|---|
| 1.001 | Cl | H | H | CH₃ | OCH₃ | N | 174–176 |
| 1.002 | Cl | CH₃ | H | CH₃ | OCH₃ | N |  |
| 1.003 | Cl | H | H | CH₃ | OCH₃ | CH | 159–161 |
| 1.004 | Cl | H | H | ◁ | OC₂H₅ | N |  |
| 1.005 | Cl | H | H | ◁ | OCH₃ | N |  |
| 1.006 | Cl | H | H | C₂H₅ | OCH₃ | N |  |
| 1.007 | Cl | H | H | CH₃ | OC₂H₅ | N |  |
| 1.008 | F | H | H | CH₃ | OCH₃ | N | 189–190 |
| 1.009 | F | CH₃ | H | CH₃ | OCH₃ | N |  |
| 1.010 | F | H | H | CH₃ | OCH₃ | CH | 170–174 |
| 1.011 | F | H | H | CH₃ | OC₂H₅ | N |  |
| 1.012 | F | H | H | ◁ | OC₂H₅ | N |  |
| 1.013 | F | H | H | ◁ | CH₃ | CH |  |
| 1.014 | F | H | H | ◁ | OCH₃ | N |  |
| 1.015 | F | H | H | C₂H₅ | OCH₃ | N |  |
| 1.016 | F | H | H | NHCH₃ | OC₂H₅ | N |  |
| 1.017 | F | H | H | N(CH₃)₂ | OCH₃ | N |  |
| 1.018 | F | H | H | N(CH₃)₂ | OCH₂CF₃ | N |  |
| 1.019 | F | H | H | Cl | OCH₃ | N |  |
| 1.020 | F | H | H | OCHF₂ | OCHF₂ | CH |  |
| 1.021 | F | H | H | OCH₃ | OCH₃ | N | 162–167 |
| 1.022 | F | H | H | OCH₃ | OCH₃ | CH | 179–181 |
| 1.023 | F | H | H | Cl | OCH₃ | CH | 154–160 |
| 1.024 | F | H | H | OCHF₂ | OCH₃ | CH | 170–172 |

BIOLOGICAL EXAMPLES

In order to investigate the herbicidal activity of the compounds of the present Application in comparison with compounds of the prior art (EP-A-0 044 808) the following Examples B1 and B2 were carried out:

EXAMPLE B 1

Preemergence herbicidal action

In a greenhouse, immediately after the test plants (Amarantus, Chenopodium, Sinapis, Stellaria, Chrysanthemum, Galium and Veronica) have been sown in seed trays, the surface of the soil is treated with an aqueous spray mixture in an amount corresponding to a rate of application of 30 g or 8 g of test compound/hectare. The seed trays are kept in the greenhouse at 22°–25° C. and 45–60% relative humidity.

After 3 weeks, the herbicidal action is evaluated according to a scale of nine ratings in comparison with an untreated control group:

1: plants have not germinated or are completely withered
2-3: very pronounced action
4-6: medium action
7-8: weak action
9: no action (as untreated control)

The compounds tested are:

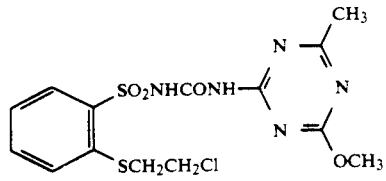

Compound A (No. 391 of EP-A-0 044 808)

against:

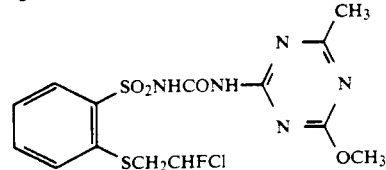

No. 1.001 of the present application, and

-continued

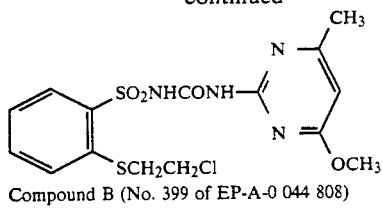

Compound B (No. 399 of EP-A-0 044 808)

against:

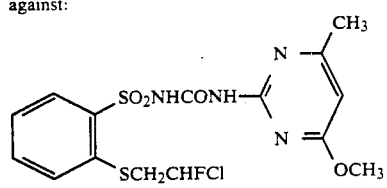

No. 1.003 of the present Application.

The results are indicated in Tables T1 and T2:

TABLE T1

| Preemergence herbicidal action with 30 g a.i./ha: | | | | |
|---|---|---|---|---|
| Test plant | Comp. A | Comp. 1.001 | Comp. B | Comp. 1.003 |
| Amarantus | 5 | 2 | 5 | 3 |
| Chenopodium | 9 | 2 | 5 | 2 |
| Sinapis | 8 | 2 | 8 | 2 |
| Stellaria | 9 | 2 | 9 | 2 |
| Chrysanth. | 9 | 2 | 5 | 2 |
| Galium | 9 | 3 | 9 | 2 |

TABLE T2

| Preemergence herbicidal action with 8 g a.i./ha: | | |
|---|---|---|
| Test plant | Comp. B | Comp. 1.003 |
| Amarantus | 9 | 7 |
| Sinapis | 9 | 3 |
| Stellaria | 9 | 2 |
| Chrysanth. | 9 | 2 |
| Galium | 9 | 3 |
| Veronica | 5 | 2 |

In this test, the herbicidal activity of the compounds of the present Application proves to be distinctly superior to that of the compounds of the prior art.

EXAMPLE B2

Postemergence herbicidal action (contact herbicide)

A number of weeds (Amarantus, Chenopodium, Sinapis, Stellaria, Chrysanthemum, Galium, Viola tricolor and Veronica) are sprayed postemergence (in the 4- to 6-leaf stage) with an aqueous active ingredient dispersion at a rate of 8 or 30 g of test compound per hectare and kept at 22°-25° C. and 45-60% relative humidity. The test is evaluated 15 days after the treatment according to a scale of nine ratings in comparison with an untreated control group:
1: plants have not germinated or are completely withered
2-3: very pronounced action
4-6: medium action
7-8: weak action
9: no action (as untreated control)

The results are indicated in Tables T3 and T4:

TABLE T3

| Postemergence herbicidal action with 8 g a.i./ha: | | |
|---|---|---|
| Test plant | Comp. A | Comp. 1.001 |
| Amarantus | 9 | 3 |

TABLE T3-continued

| Postemergence herbicidal action with 8 g a.i./ha: | | |
|---|---|---|
| Test plant | Comp. A | Comp. 1.001 |
| Chenopodium | 9 | 4 |
| Sinapis | 9 | 3 |
| Stellaria | 9 | 3 |
| Chrysanth. | 9 | 5 |
| Galium | 9 | 8 |
| Viola t. | 9 | 7 |
| Veronica | 9 | 7 |

TABLE T4

| Postemergence herbicidal action with 30 g a.i./ha: | | | | |
|---|---|---|---|---|
| Test plant | Comp. A | Comp. 1.001 | Comp. B | Comp. 1.003 |
| Amarantus | 7 | 2 | — | — |
| Chenopodium | 9 | 3 | 8 | 6 |
| Sinapis | 3 | 2 | 4 | 2 |
| Stellaria | 3 | 2 | — | — |
| Chrysanth. | 4 | 3 | — | — |
| Galium | 6 | 3 | 7 | 6 |
| Viola t. | 9 | 4 | 4 | 7 |
| Veronica | 9 | 7 | — | — |

In the case of postemergence application too, the compounds of formula I according to the present Application exhibit better herbicidal activity than do the comparison compounds of the prior art.

EXAMPLE B3

Herbicidal action in wild rice (paddy rice)

The weeds Echinochloa crus galli and Monocharia vag., which occur in water, are sown in plastic beakers (surface: 60 cm²; volume: 500 ml). After sowing, the beakers are filled with water up to the surface of the soil. 3 days after sowing, the water level is increased to slightly above the soil surface (3-5 mm). Application is effected 3 days after sowing by spraying the beakers with the test compounds. The rate of application corresponds to a concentration of 8-500 g of active ingredient per hectare. The beakers are then kept in the greenhouse under optimum growth conditions for rice weeds, i.e. at 25°-30° C. and at high humidity.

The evaluation of the tests takes place 3 weeks after application. The compounds of formula I damage the weeds.

| Formulation Examples for active ingredients of formula I(throughout, percentages are by weight) | | | |
|---|---|---|---|
| 1. Wettable powders | a) | b) | c) |
| compound of formula I | 20% | 50% | 0.5% |
| sodium lignosulfonate | 5% | 5% | 5% |
| sodium laurylsulfate | 3% | — | — |
| sodium diisobutylnaphthalene-sulfonate | — | 6% | 6% |
| octylphenol polyethylene glycol ether (7-8 mol of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| 2. Emulsifiable concentrates | a) | b) |
| --- | --- | --- |
| compound of formula I | 10% | 1% |
| calcium dodecylbenzenesulfonate | 3% | 3% |
| octylphenol polyethylene glycol ether (4-5 mol of ethylene oxide) | 3% | 3% |
| castor oil polyethylene glycol ether (36 mol of ethylene oxide) | 4% | 4% |
| cyclohexanone | 30% | 10% |
| xylene mixture | 50% | 79% |

Emulsions of any required concentration can be obtained from such concentrates by dilution with water.

| 3. Dusts | a) | b) |
| --- | --- | --- |
| compound of formula I | 0.1% | 1% |
| talcum | 99.9% | — |
| kaolin | — | 99% |

Ready-for-use dusts are obtained by intimately mixing the carriers with the active ingredient.

| 4. Extruder granules | a) | b) |
| --- | --- | --- |
| compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is moistened with water. The mixture is extruded and then dried in a stream of air.

| 5. Coated granules | |
| --- | --- |
| compound of formula I | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 6. Suspension concentrate | a) | b) |
| --- | --- | --- |
| compound of formula I | 5% | 40% |
| ethylene glycol | 10% | 10% |
| nonylphenol polyethylene glycol ether (15 mol of ethylene oxide) | 1% | 6% |
| sodium lignosulfonate | 5% | 10% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 77% | 32% |

The finely ground active ingredient is intimately mixed with the adjuvants, giving a suspension concentrate from which suspensions of any desired concentration can be obtained by dilution with water.

| 7. Salt solution | |
| --- | --- |
| compound of formula I | 5% |
| isopropylamine | 1% |
| octylphenol polyethylene glycol ether (78 mol of ethylene oxide) | 3% |

-continued

| 7. Salt solution | |
| --- | --- |
| water | 91% |

The compounds of formula I are used in unmodified form or, preferably, as compositions together with the adjuvants conventionally employed in formulation technology, and are therefore formulated in known manner e.g. into emulsifiable concentrates, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, scattering or pouring are chosen in accordance with the intended objectives and the prevailing circumstances.

What is claimed is:

1. An N-phenylsulfonyl-N'-pyrimidinyl-urea of formula I

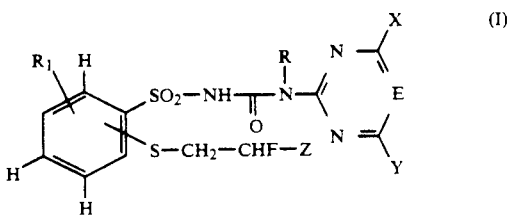

wherein

R is hydrogen or $C_1$-$C_4$alkyl, $R_1$ is hydrogen, halogen, $C_1$-$C_5$alkyl, $C_2$-$C_5$alkenyl, $C_1$-$C_4$haloalkyl, COO—$R_2$ or A—$R_3$;

$R_2$ is $C_1$-$C_5$alkyl;

$R_3$ is $C_1$-$C_5$alkyl, $C_2$-$C_4$alkoxyalkyl or $C_1$-$C_5$haloalkyl;

X is $C_1$-$C_3$alkyl, $C_1$-$C_3$alkyl mono- to tri-substituted by halogen; $C_1$-$C_3$alkoxy or $C_1$-$C_3$alkoxy mono- to tri-substituted by halogen;

A is oxygen, sulfur, SO or $SO_2$;

Y is halogen, $C_1$-$C_3$alkyl, $C_1$-$C_3$alkyl mono- to tri-substituted by halogen; $C_1$-$C_3$alkoxy, $C_1$-$C_3$alkoxy mono- to tri-substituted by halogen; cyclopropyl, methylamino or dimethylamino;

E is or the methine group; and

Z is fluorine or chlorine;

or a salt of that compound;

wherein $R_1$ at the phenyl ring is in the 5-position and the group —S—$CH_2$—Z is in the 2-position.

2. A compound of formula I according to claim 1, wherein R is hydrogen.

3. A compound of formula I according to claim 1, wherein $R_1$ is hydrogen.

4. A compound of formula I according to claim 1, wherein X is $C_1$-$C_3$alkyl, $C_1$-$C_3$alkoxy or $C_1$-$C_3$alkoxy mono- to tri-substituted by halogen; and Y is chlorine, $C_1$-$C_3$alkyl, $C_1$-$C_3$alkoxy, cyclopropyl, or $C_1$-$C_3$alkoxy mono- to tri-substituted by halogen.

5. A compound of formula I according to claim 1, wherein X is methyl, methoxy, ethoxy or difluoromethoxy; and Y is methyl, methoxy, ethoxy, difluoromethoxy or chlorine.

6. A compound of formula I according to claim 1, wherein X is methoxy or ethoxy; and Y is methyl or methoxy.

7. A compound of formula I according to claim 3, wherein X is $C_1$-$C_3$alkyl, $C_1$-$C_3$alkoxy or $C_1$-$C_3$alkoxy mono- to tri-substituted by halogen; and Y is chlorine, $C_1$-$C_3$alkyl, $C_1$-$C_3$alkoxy, cyclopropyl, or $C_1$-$C_3$alkoxy mono- to tri-substituted by halogen.

8. A compound of formula I according to claim 7, wherein X is methyl, methoxy, ethoxy or difluoromethoxy; and Y is methyl, methoxy, ethoxy, difluoromethoxy or chlorine.

9. A compound of formula I according to claim 7, wherein X is methoxy or ethoxy; and Y is methyl or methoxy.

10. A herbicidal and plant-growth-regulating composition comprising at least a herbicidally and plant-growth-inhibitingly effective amount of a compound of the formula I according to claim 1 and an agriculturally acceptable carrier.

11. A composition according to claim 10 comprising said compound of formula I in an amount of from 0.1% to 95%.

12. A method of controlling undesirable plant growth, which comprises applying to the plants or to the locus thereof a herbicidally effective amount of a compound of formula I, according to claim 1, or of a composition comprising that compound.

13. A method according to claim 12, which comprises applying the active ingredient in an amount of from 0.001 to 2 kg per hectare.

14. A method of regulating plant growth, which comprises applying to the plants or to the locus thereof a plant-growth-inhibitingly effective amount of a compound of the formula I, according to claim 1, or of a composition comprising that compound.

15. A method according to claim 12 for the selective control of weeds in crops of useful plants.

* * * * *